(12) United States Patent
Douk et al.

(10) Patent No.: US 7,655,040 B2
(45) Date of Patent: Feb. 2, 2010

(54) CARDIAC VALVE ANNULUS REDUCTION SYSTEM

(75) Inventors: Nareak Douk, Lowell, MA (US); Nasser Rafiee, Andover, MA (US); Eliot Bloom, Hopkinton, NH (US); Douglas A. Fogg, Merrimac, MA (US); Rany Huynh, Charlestown, MA (US); David D. Barone, Lexington, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 452 days.

(21) Appl. No.: 10/531,819

(22) PCT Filed: Nov. 12, 2004

(86) PCT No.: PCT/US2004/037867

§ 371 (c)(1),
(2), (4) Date: Sep. 25, 2006

(87) PCT Pub. No.: WO2005/046488

PCT Pub. Date: May 26, 2005

(65) Prior Publication Data

US 2007/0051377 A1      Mar. 8, 2007

Related U.S. Application Data

(60) Provisional application No. 60/519,114, filed on Nov. 12, 2003.

(51) Int. Cl.
*A61F 2/24* (2006.01)

(52) U.S. Cl. ............... 623/2.11; 623/2.36; 623/2.37; 623/2.41; 623/1.11; 623/1.12; 606/151; 606/215; 606/217; 606/219

(58) Field of Classification Search ............... 623/2.11, 623/2.36–2.37, 2.41, 1.11–1.12; 606/215–217, 606/219, 151
See application file for complete search history.

(56) References Cited

U.S. PATENT DOCUMENTS

| | | | | |
|---|---|---|---|---|
| 5,478,309 A * | 12/1995 | Sweezer et al. | ............ | 604/6.14 |
| 5,492,119 A * | 2/1996 | Abrams | ............ | 600/375 |
| 5,769,812 A * | 6/1998 | Stevens et al. | ............ | 604/4.01 |
| 5,860,920 A * | 1/1999 | McGee et al. | ............ | 600/374 |
| 6,619,291 B2 | 9/2003 | Hlavka et al. | | |
| 6,629,534 B1 * | 10/2003 | St. Goar et al. | ............ | 128/898 |
| 6,669,687 B1 * | 12/2003 | Saadat | ............ | 606/14 |
| 6,689,164 B1 * | 2/2004 | Seguin | ............ | 623/2.36 |

(Continued)

FOREIGN PATENT DOCUMENTS

WO       WO01/00114       1/2001

*Primary Examiner*—Darwin P Erezo
*Assistant Examiner*—Son Dang

(57) ABSTRACT

A catheter-based, annulus reduction device and system for cardiac valve repair and method of using the same. The system is usable for treating mitral valve regurgitation and comprises a catheter, a reduction ring carried within the catheter, the reduction ring including a plurality of exit ports formed in a side wall of the reduction ring and filament received in the reduction ring. The filament includes a plurality of radially extendible barbs corresponding to the sidewall openings. The reduction ring carrying the filament is deployed adjacent a mitral valve annulus and the filament is translated relative to the reduction ring to deploy the barbs through the exit ports and into the annulus and to further translate the reduction ring with deployed barbs to reshape the annulus.

24 Claims, 14 Drawing Sheets

U.S. PATENT DOCUMENTS

| | | |
|---|---|---|
| 6,702,826 B2 | 3/2004 | Liddicoat et al. |
| 7,226,477 B2 * | 6/2007 | Cox .......................... 623/2.37 |
| 7,485,142 B2 * | 2/2009 | Milo .......................... 623/2.11 |
| 7,563,273 B2 * | 7/2009 | Goldfarb et al. ............ 606/213 |
| 2002/0156526 A1 | 10/2002 | Hlavka et al. |
| 2002/0183837 A1 * | 12/2002 | Streeter et al. ............. 623/2.11 |
| 2003/0220685 A1 | 11/2003 | Hlavka et al. |
| 2004/0210304 A1 * | 10/2004 | Seguin et al. ............... 623/2.11 |
| 2005/0038506 A1 * | 2/2005 | Webler et al. ............... 623/2.11 |
| 2005/0060030 A1 * | 3/2005 | Lashinski et al. ........... 623/2.37 |
| 2006/0122633 A1 * | 6/2006 | To et al. ...................... 606/139 |
| 2006/0129188 A1 * | 6/2006 | Starksen et al. ............. 606/232 |
| 2007/0027533 A1 * | 2/2007 | Douk ........................ 623/2.11 |
| 2007/0043435 A1 * | 2/2007 | Seguin et al. ............... 623/2.11 |
| 2007/0129758 A1 * | 6/2007 | Saadat ........................ 606/232 |

* cited by examiner

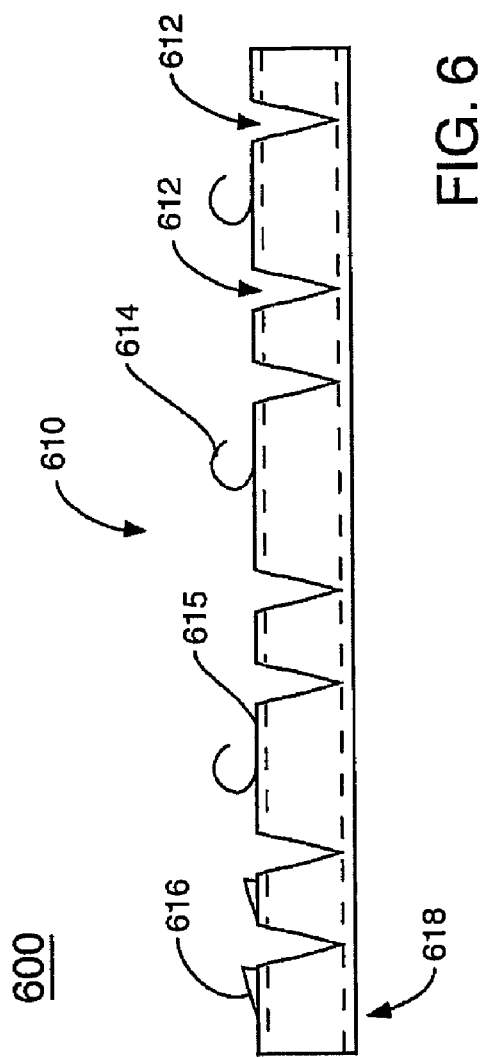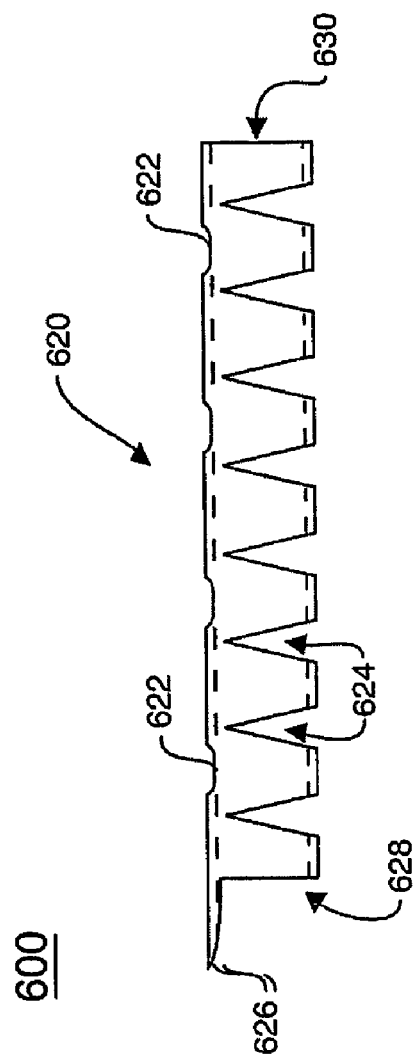

1900

2000

2100

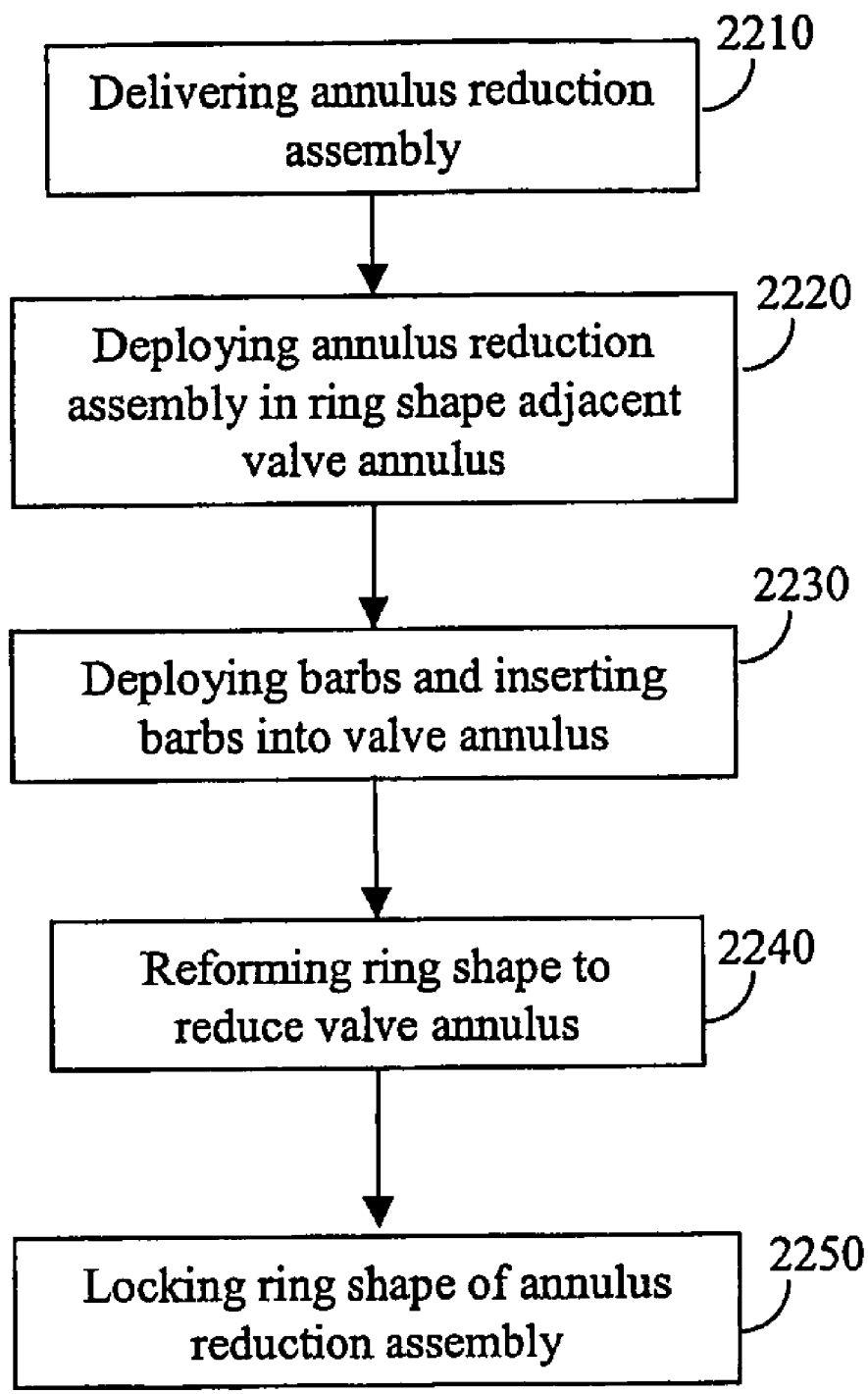

CARDIAC VALVE ANNULUS REDUCTION SYSTEM

TECHNICAL FIELD

The technical field of this disclosure is medical devices, particularly, a cardiac valve annulus reduction system and method of using the same.

BACKGROUND OF THE INVENTION

Heart valves, such as the mitral valve, tricuspid, aortic and pulmonic valves, are sometimes damaged by disease or by aging, which can cause problems with the proper function of the valve. Heart valve problems generally take one of two forms: stenosis, in which a valve does not open completely or the opening is too small, resulting in restricted blood flow; or insufficiency, in which blood leaks backward across the valve that should be closed. Valve replacement may be required in severe cases to restore cardiac function. In common practice, repair or replacement requires open-heart surgery with its attendant risks, expense, and extended recovery time. Open-heart surgery also requires cardiopulmonary bypass with risk of thrombosis, stroke, and infarction.

In various types of cardiac disease, mitral valve insufficiency may result. Any one or more of the mitral valve structures, i.e., the anterior and posterior leaflets, the chordae, the papillary muscles or the annulus may be compromised by damage from disease or injury, causing the mitral valve insufficiency. Typically, in cases where there is mitral valve insufficiency, there is some degree of annular dilation resulting in mitral valve regurgitation. Mitral valve regurgitation occurs as the result of the leaflets being moved back from each other by the dilated annulus, thus making the leaflets unable to appose each other completely during systole. Thus, without correction, the mitral valve insufficiency may lead to disease progression and/or further enlargement and worsening of the insufficiency. In some instances, correction of the regurgitation may not require repair of the valve leaflets themselves, but simply a reduction in the size of the annulus.

A variety of techniques have been attempted to reduce the diameter of the mitral annulus and eliminate or reduce valvular regurgitation in patients with incompetent valves. Current surgery to correct mitral regurgitation in humans includes a number of mitral valve replacement and repair techniques.

Valve replacement can be performed through open-heart surgery, open chest surgery, or percutaneously. The native valve is removed and replaced with a prosthetic valve, or a prosthetic valve is placed over the native valve. The valve replacement may be a mechanical or biological valve prosthesis. The open chest and percutaneous procedures avoid opening the heart and cardiopulmonary bypass. However, the valve replacement may result in a number of complications including a risk of endocarditis. Additionally, mechanical valve replacement requires subsequent anticoagulation treatment to prevent thromboembolisms.

As an alternative to valve replacement, various valve repair techniques have been used including quadrangular segmental resection of a diseased posterior leaflet; transposition of posterior leaflet chordae to the anterior leaflet; valvuloplasty with plication and direct suturing of the native valve; substitution, reattachment or shortening of chordae tendinae; and annuloplasty in which the effective size of the valve annulus is contracted by attaching a prosthetic annuloplasty ring to the endocardial surface of the heart around the valve annulus. The annuloplasty techniques may be used in conjunction with other repair techniques. Typically such rings are sutured along the posterior mitral leaflet adjacent to the mitral annulus in the left atrium. The rings either partially or completely encircle the valve, and may be rigid or flexible/non-elastic. All of these procedures require cardiopulmonary bypass, though some less and minimally invasive techniques for valve repair and replacement are being developed.

Although mitral valve repair and replacement can successfully treat many patients with mitral valve insufficiency, techniques currently in use are attended by significant morbidity and mortality. Most valve repair and replacement procedures require a thoractomy to gain access into the patient's thoracic cavity. Surgical intervention within the heart generally requires isolation of the heart and coronary blood vessels from the remainder of the arterial system and arrest of cardiac function. Open chest techniques with large sternum openings are typically used. Those patients undergoing such techniques may have scarring retraction, tears or fusion of valve leaflets as well as disorders of the subvalvular apparatus.

Recently, other surgical procedures have been provided to reduce the mitral valve annulus using a less invasive surgical technique. According to one method, a prosthesis is transvenously advanced into the coronary sinus and deployed within the coronary sinus to reduce the diameter of the mitral valve annulus. The prosthesis is tightened down within the coronary sinus to reduce the mitral valve annulus. This may be accomplished in an open surgical procedure or by percutaneous transluminal access through the venous system by one of the internal jugular, subclavian or femoral veins.

While the coronary sinus implant provides a less invasive treatment alternative, the placement of the prosthesis within the coronary sinus may be problematic for a number of reasons. Sometimes the coronary sinus is not accessible. The coronary sinus on a particular individual may not wrap around the heart far enough to allow enough encircling of the mitral valve. Also, leaving a device in the coronary sinus may result in formation and release of thrombus that may pass into the right atrium, right ventricle and ultimately into the lungs, possibly causing a pulmonary embolism. Another disadvantage is that the coronary sinus is typically used for placement of a pacing lead, which may be precluded by the previous placement of a prosthesis in the coronary sinus.

It would be desirable, therefore, to provide a method and device for reducing cardiac valve regurgitation that would overcome these and other disadvantages.

SUMMARY OF THE INVENTION

One aspect of the present invention provides a cardiac valve annulus reduction system to provide catheter based valve repair. The system for treating mitral valve regurgitation comprises a catheter, a tubular member carried within the catheter, the tubular member including a plurality of openings formed in a sidewall of the tubular member and an barb assembly received in the tubular member. The barb assembly includes a plurality of radially extendible barbs corresponding to the sidewall openings. The tubular member carrying the barb assembly is deployed adjacent a mitral valve annulus and the barb assembly is translated relative to the tubular member to deploy the barbs through the sidewall openings and into the annulus and to further translate the tubular member with deployed barbs to reshape the annulus.

Another aspect of the invention provides a method for treating mitral valve regurgitation. The method comprises deploying a tubular member carrying an barb assembly adjacent a mitral valve annulus via a catheter, translating the barb assembly relative to the tubular member, inserting barb portions of the barb assembly through tubular member sidewall openings and into the annulus responsive to the translation and translating the inserted barbs and tubular member with the barb assembly to reshape the annulus.

Another aspect of the invention provides a system for treating mitral valve regurgitation. The system comprises means for reducing a mitral valve annulus, means for translating a barb assembly relative to a tubular member, means for inserting barb portions of the barb assembly through tubular member sidewall openings and into the annulus responsive to the translation and means for locking the barb assembly relative to the tubular member.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 6-7 show detailed views of a reduction ring and barb assembly for a cardiac valve annulus reduction assembly in accordance with the present invention;

FIG. 23 shows a flow chart for a method of implanting a cardiac valve annulus reduction assembly in accordance with the present invention.

DETAILED DESCRIPTION OF THE PRESENTLY PREFERRED EMBODIMENT

Figure 1:
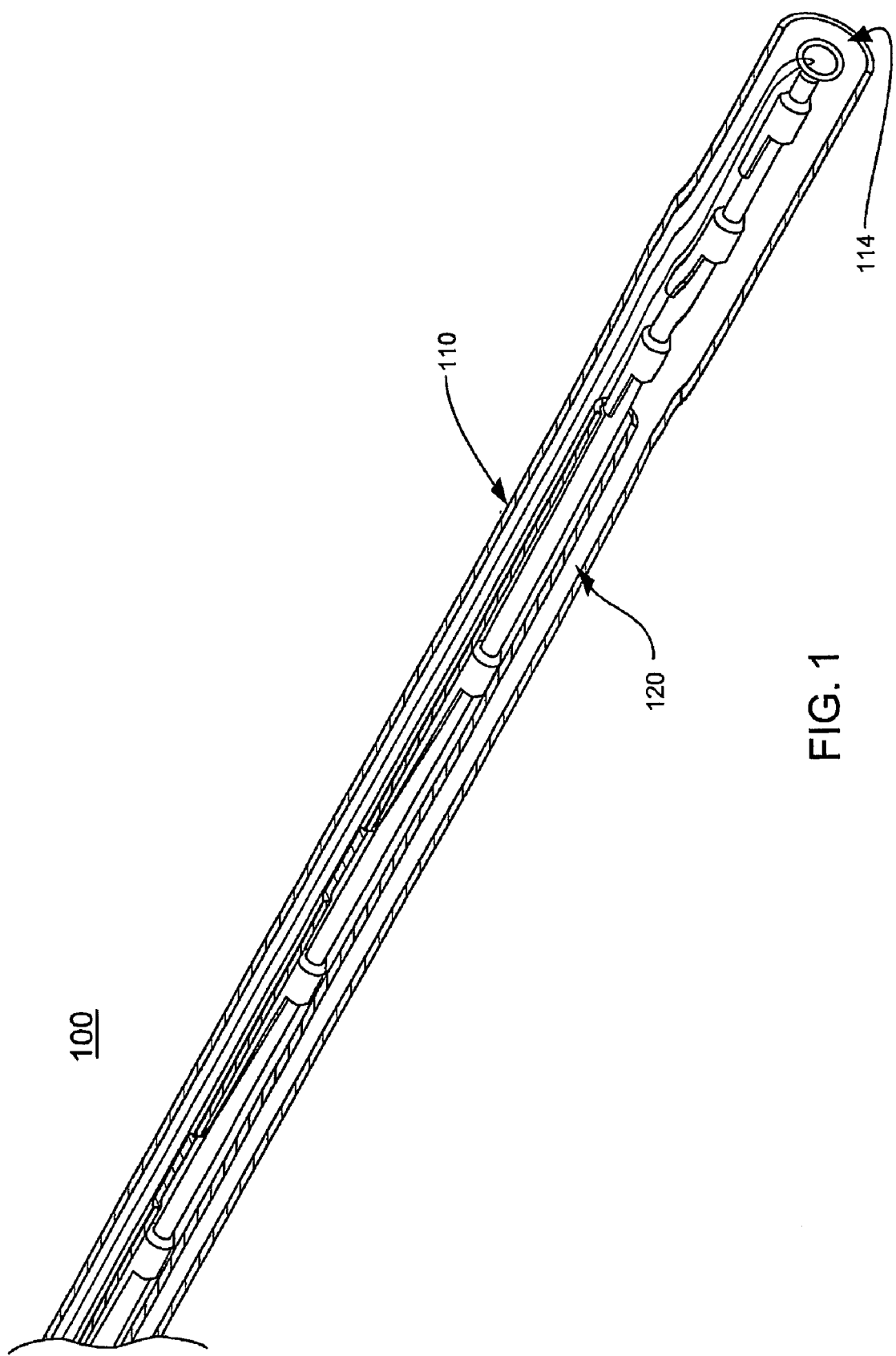
FIG. 1 shows a cardiac valve annulus reduction delivery system in accordance with the present invention.

FIG. 1 shows a cardiac valve annulus reduction assembly and a delivery system in accordance with the present invention. Annulus reduction delivery system 100 includes delivery catheter 110 having lumen 114 there through. Annulus reduction assembly 120 is disposed within lumen 114 and is described in more detail below.

Figure 2:
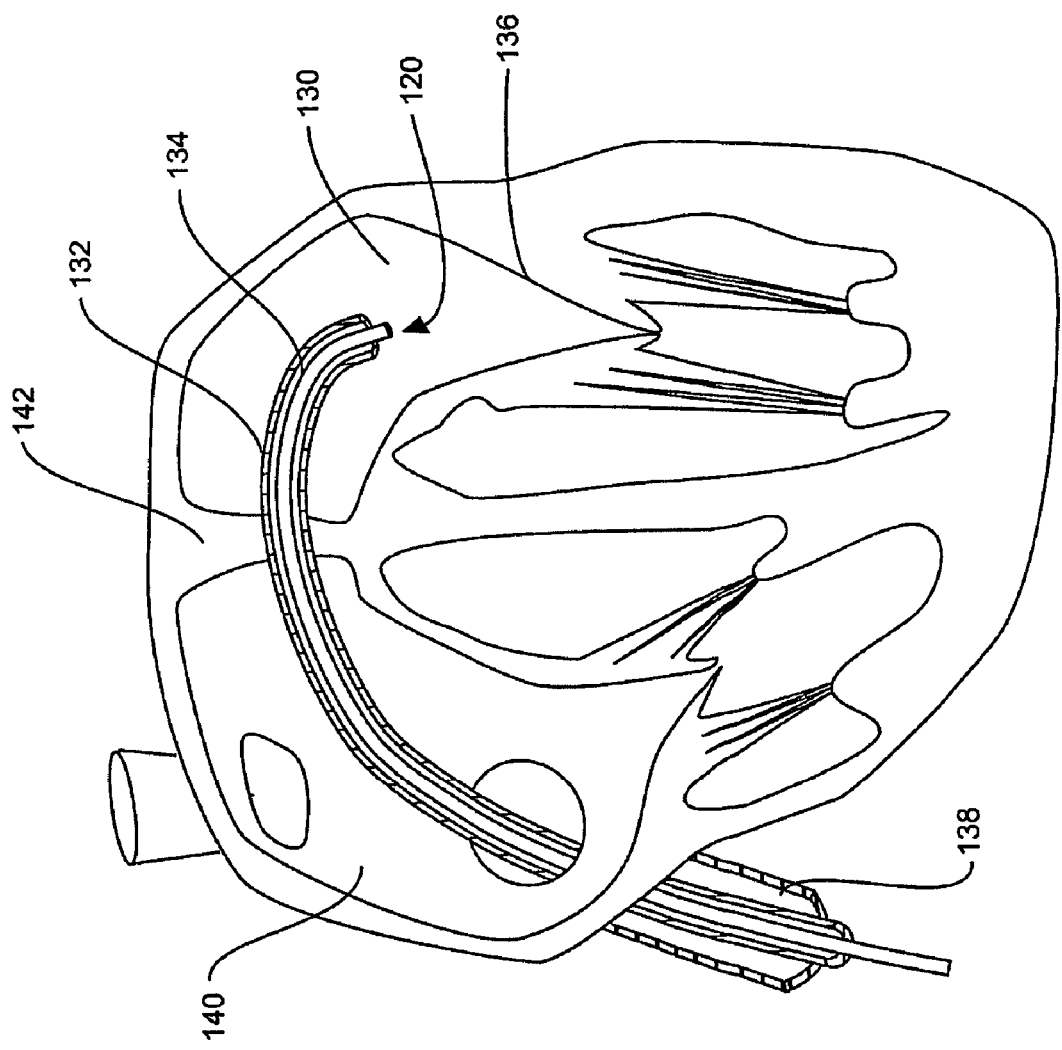
FIG. 2 shows a cardiac valve annulus reduction delivery system positioned within the left atrium in accordance with the present invention.

FIG. 2 shows a delivery system 100 positioned via a femoral venous transeptal approach with the system distal end lying within the left atrium. As shown, annulus reduction assembly 120 has not been deployed from delivery catheter 110. Annulus reduction assembly 120 may be delivered via percutaneous transluminal techniques or via surgery using open-chest or port access modalities.

For the exemplary case of mitral valve remodeling shown in FIGS. 1 and 2, annulus reduction assembly 120 is implanted from the left atrium 130. An elongate element 132, such as a catheter having lumen 134, is first inserted to provide a path for annulus reduction delivery system 100 from the exterior of the patient to left atrium 130. Annulus reduction delivery system 100 can then be advanced through lumen 134 so that annulus reduction assembly 120 is located at mitral valve annulus 136 for deployment. FIG. 2 illustrates a transeptal approach through the vena cava. For this approach, elongate element 132 is inserted into the femoral vein and passed through the common iliac vein, inferior vena cava 138 and into right atrium 140. Next, atrial septum 142 is punctured with a guide wire or other puncturing device, and the distal end of elongate element 132 is advanced into left atrium 130. Annulus reduction assembly 120 may then be advanced through lumen 134 of elongate element 132 to the mitral valve for implantation. In one embodiment, elongate element 132 is a puncture catheter, as are well known in the art, configured to pierce the atrial septal wall. The delivery method may also include a dilator catheter for providing a larger diameter pathway for delivering annulus reduction delivery system 100. The terms "distal" and "proximal" are used herein with reference to the treating clinician during deployment of the device; "Distal" indicates a portion distant from, or a direction away from the clinician and "proximal" indicates a portion near to, or a direction towards the clinician.

Those skilled in the art will appreciate that alternative paths are available to gain access to the left atrium. For example, another possible path would be via insertion into the radial vein, then through the brachial vein, the subclavian vein and the superior vena cava into the right atrium, and then transeptally into the left atrium. Another possible path would be through the femoral artery into the aorta, through the aortic valve into the left ventricle, and then through the mitral valve into the left atrium. Yet another possible path would be via port access into the left or right pulmonary vein and directly into the left atrium. For surgical approaches with an open chest, the elongate element can be a trocar or cannula inserted directly in the vena cava or the aortic arch. Elongate element 132 can then follow the same path as the percutaneous transluminal procedure to reach the left atrium, either transeptally or through the cardiac valves. Transeptal approaches, whether percutaneous or surgical, may require placement of a closure device at the transeptal puncture on removal of the elongate element after the procedure. Similar transluminal or surgical approaches can be used to access the other cardiac valves, if an annulus reduction assembly is to be implanted on a cardiac valve other than the mitral valve.

Figure 3:
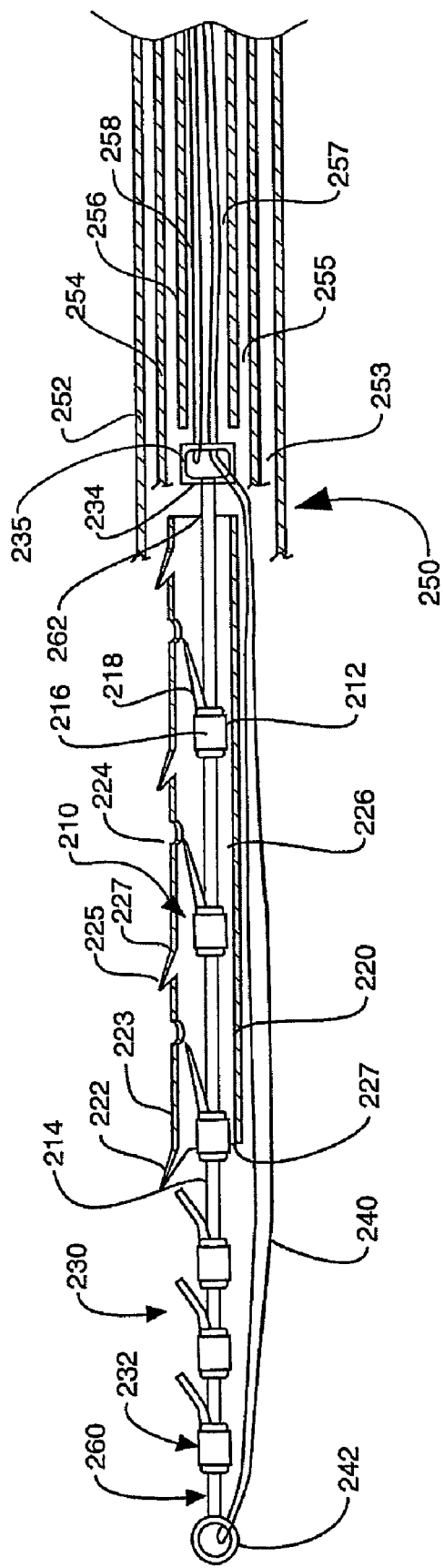
FIG. 3 shows a cardiac valve annulus reduction assembly in accordance with the present invention.

FIG. 3 shows one embodiment of an annulus reduction assembly 200 in accordance with the present invention. Annulus reduction assembly 200 includes barb assembly 210, reduction ring 220, locking assembly 230 and reshaping cord 240. FIG. 3 also illustrates annulus reduction delivery system 250, which will be described in detail below. Annulus reduction assembly 200 is shown in a delivery configuration as it would appear disposed within lumen 253 of delivery catheter 252 before deployment at the valve annulus.

Reduction ring 220 comprises a tubular member 226 having through lumen 227. Reduction ring 220 includes a plurality of barb exit ports 224 and temporary barb 222. Reduction ring 220 is composed of a flexible, biocompatible implant material including a metallic base or a polymeric base, such as stainless steel, nitinol, platinum alloy, titanium, chromium-based alloy, cobalt-based alloy, thermoplastic or thermoset polymer, or a combination thereof. Exit port 224 may be any shape and size to allow the passage of barb penetrating member 218. In one embodiment, exit port 224 is oval.

Exit ports 224 are positioned on reduction ring 220 such that, when annulus reduction assembly 200 is deployed, exit ports 224 are adjacent the valve annulus. The plurality of exit ports 224 may be linearly aligned along one side of reduction ring 220 such that, when annulus reduction assembly 200 is formed into a general ring shape adjacent the valve annulus, exit ports 224 may be arranged along the outer diameter or perimeter of the ring, in the plane of the ring. Alternatively, when annulus reduction assembly 200 is formed into a general ring shape, exit ports 224 may be arranged adjacent the outer diameter or perimeter of the ring, with ports 224 being oriented at least slightly towards the valve leaflets at an acute angle from the plane of the ring. In the latter alternative embodiment, barb penetrating members 218 exiting from ports 224 in generally ring-shaped annulus reduction assembly 200 are positioned in a generally conical arrangement.

Reduction ring 220 further includes temporary barb 222 positioned at reduction ring distal end 223. Temporary barb 222 may be used to provide stability during the first stages of the implantation procedure, as by temporarily holding reduction ring 220 at the implantation site before insertion of barb penetrating members 218 into the valve annulus. Reduction ring 220 may also include a plurality of anchors 225 disposed along and protruding from reduction ring outer surface 228. Anchors 225 provide additional anchoring of the implanted ring to the valve annulus and are linearly positioned on outer surface 228 that will be adjacent the valve annulus.

Barb assembly 210 is movably disposed within lumen 227 of tubular member 226. Barb assembly 210 includes filament 214 and a plurality of radially self-extending barbs 212 securely attached to filament 214. Filament 214 can be made of any biocompatible metal or polymer that can be formed into a ring shape when deployed at the cardiac valve annulus. In one embodiment, filament 214 is a braided polyester cord. In another embodiment, filament 214 is stainless steel or another metallic wire. Each barb 212 is positioned adjacent a corresponding exit port 224 of tubular member 226. Barbs 212 comprise a barb body 216 and a radially self-extending, tissue-penetrating portion 218. Tubular member 226 restrains barbs 212 until barb assembly 210 is translated within tubular member 226 to allow tissue-penetrating portions 218 to extend through exit ports 224. Barbs 212 may be fixedly attached to filament 214 via barb body 216 using a crimp, an adhesive or any other method of attachment well known in the art. In one embodiment, barbs 214 and filament 214 are fashioned from the same piece of material. In one embodiment, penetrating portion 218 is composed of shape memory material such as nitinol. Alternatively, penetrating portion 218 may comprise another metal such as stainless steel, cobalt-based alloy or combinations thereof. The number and position of barbs 212 and corresponding exit ports 224 may vary depending on the intended result.

Figure 12:
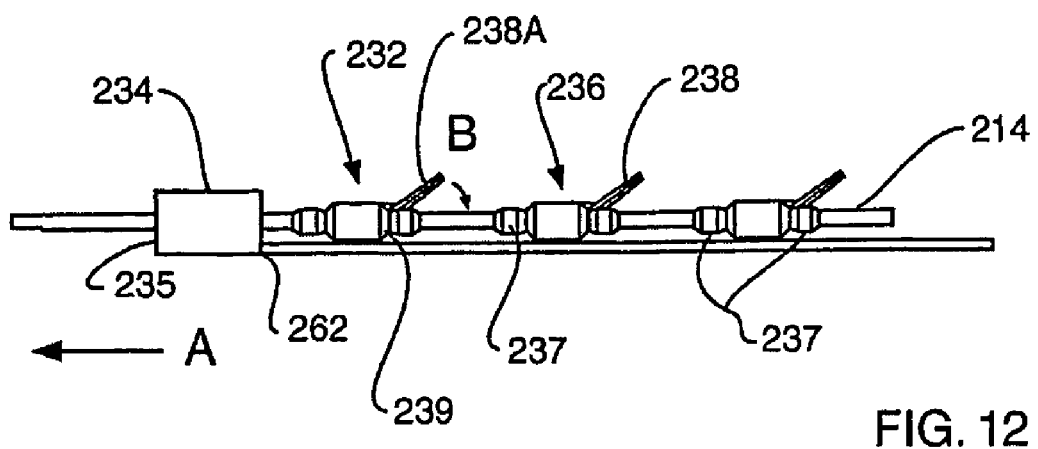
FIGS. 12-13 show detailed views of a lock mechanism for a cardiac valve annulus reduction assembly in accordance with the present invention.
Figure 13:
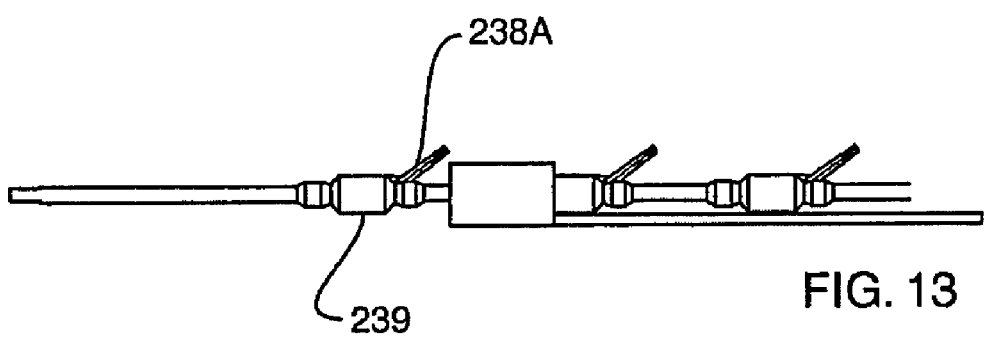

Locking assembly 230 includes a plurality of key members 232 and lock 234 that function similarly to a ratchet and pawl mechanism. Key members 232 and lock 234 are disposed at opposite ends of filament 214. Key members 232 are serially attached along filament distal end 260 and lock 234 is attached to filament proximal end 262. FIGS. 12-13 illustrate locking assembly 230 in greater detail.

Referring to FIGS. 12-13, each key member 232 comprises key body 236 having deflectable tab 238. Key bodies 236 are disposed on filament 214 in a spaced apart manner using a crimp, an adhesive or any other method of attachment known in the art. Key bodies 236 may be composed of biocompatible metal, polymer or combinations thereof. Tab 238 normally forms an acute angle with filament 214 and is elastically deformable towards filament 214 to allow movement of key member 232 through lock 234 in only one direction. Movement of key member 232 through lock 234 in the opposite direction is prevented by the resistance of tab 238 to deformation away from filament 214. Such reverse movement, or unlocking, is also prevented because tab 238 would have to fold over key body 236, creating a combined transverse dimension that will not fit through lock lumen 235. Deflectable tab 238 may be composed of biocompatible metal, polymer or combinations thereof. Deflectable tab 238 may be integrally formed with, or attached to key body 236 by welding, crimping, adhesive, or any other method known to those with skill in the art.

In one embodiment, locking assembly 230 may also include a plurality of stops 237. In one embodiment, a stop 237 is positioned on either side of key body 236 and securely attached to filament 214 to prevent movement of key member 232 along filament 214. Lock 234 may be composed of biocompatible metal, polymer or combinations thereof. FIGS. 12 and 13 illustrate movement of a first key member 232 through lumen 235 of lock 234. As filament 214 is pulled in the direction of arrow A, first key member 239 passes through lock lumen 235. As first key member 239 passes through lumen 235, deflectable tab 238A deflects in the direction of arrow B. Upon exiting lumen 235, deflectable tab 238A will elastically return to the non-deflected position, from which it can prevent movement of lock 234 and filament 214 in the opposite direction.

Returning to FIG. 3, annulus reduction assembly 200 includes reshaping cord 240 looped through cord ring 242 disposed at filament distal end 260. Both ends (not shown) of reshaping cord 240 are further threaded through lock lumen 235. In one embodiment, reshaping cord 240 comprises a string or cord-like material having sufficient length such that both ends extend through annulus reduction delivery system 250 and out of the patient for manipulation by the clinician. Reshaping cord 240 is configured so that the cord may be removed from the vasculature after implantation of annulus reduction assembly 200. In one embodiment, reshaping cord 240 comprises a tether.

FIG. 3 further illustrates annulus reduction delivery system 250. Annulus reduction delivery system 250 includes a plurality of coaxially arranged tubular components, as follows. Delivery catheter 252 has lumen 253; Ring holding tube 254 has lumen 255 and is disposed within lumen 253: Lock holding tube 256 has lumen 257 and is disposed within lumen 255. Annulus reduction delivery system 250 further includes actuator cord 258, which is similar to reshaping cord 240. Actuator cord 240 is releasably connected to lock 234. In one embodiment, actuator cord 258 is looped through lock 234 and has both ends extend to a point out side of the patient. Annulus reduction delivery system 250 is described in detail below with reference to method 2200 and FIG. 22.

Figure 4:
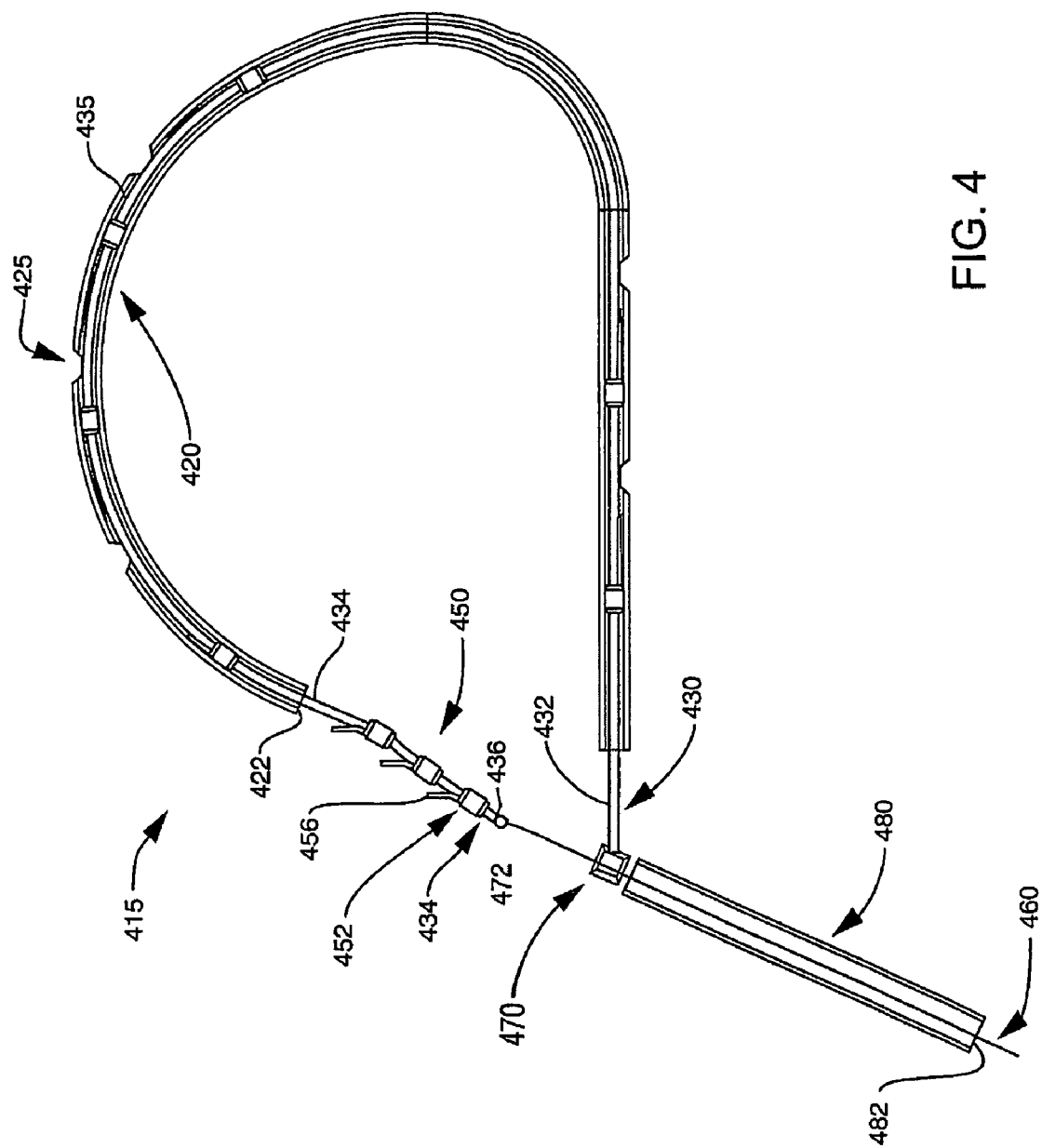
FIGS. 4-5 show another embodiment of a cardiac valve annulus reduction assembly in accordance with the present invention.
Figure 5:
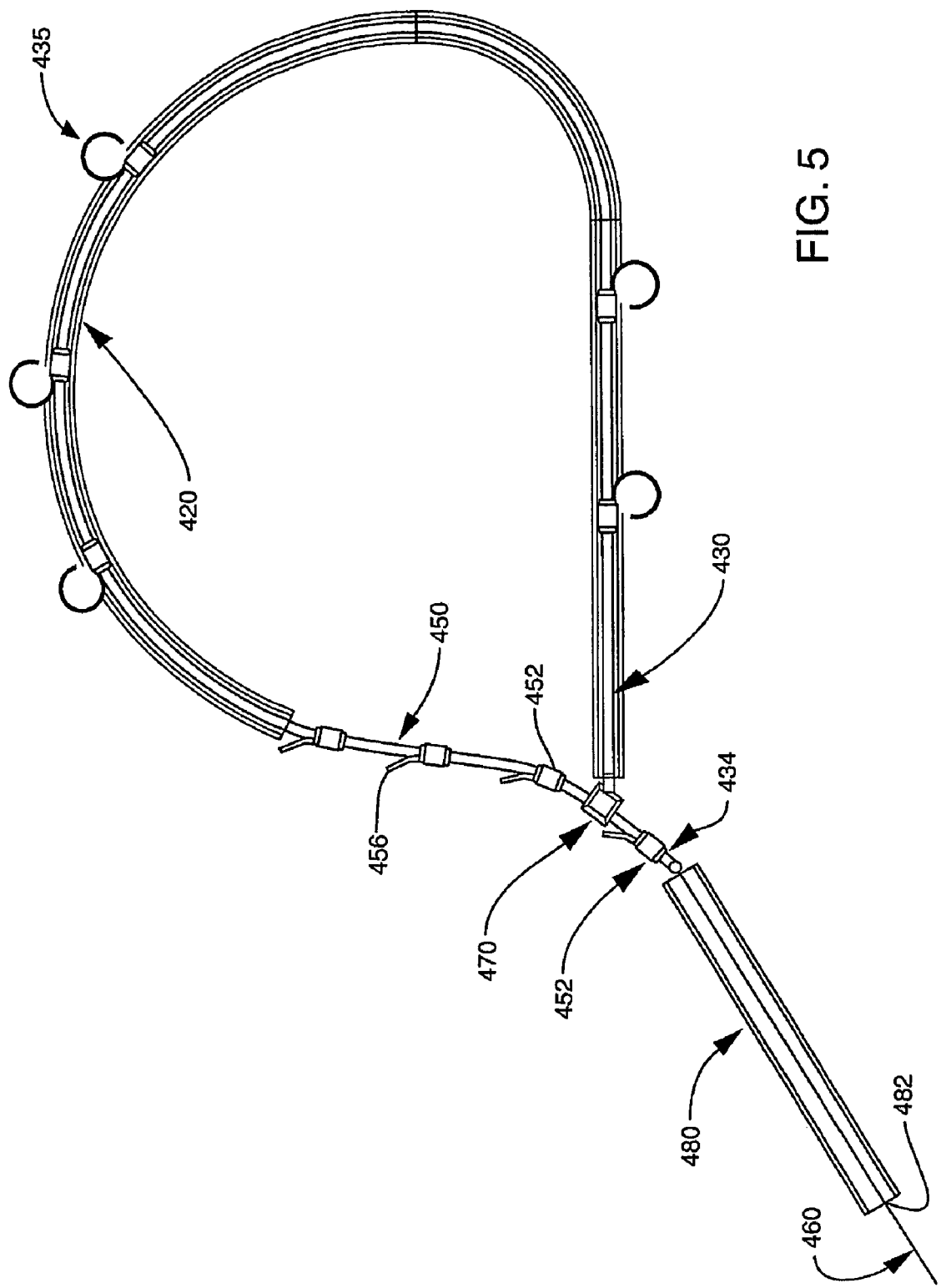

FIGS. 4-5 illustrate another embodiment of a cardiac valve annulus reduction system in accordance with the present invention. FIG. 4 shows a detailed view of annulus reduction assembly 415. Annulus reduction assembly 415 includes reduction ring 420, filament 430, locking assembly 450 and reshaping cord 460.

Reduction ring 420 includes a plurality of exit ports 425 and lumen 422. Filament 430 is disposed within lumen 422 of reduction ring 420. Filament 430 includes a plurality of barbs 435 positioned adjacent exit ports 425. Barbs 435 may be composed of materials such as nitinol, cobalt based alloy, stainless steel, or combinations thereof. Filament 430 also includes proximal end 432 and distal end 434. Proximal end 432 is secured to lock 470, as best seen in FIG. 4.

Locking assembly 450 is attached to filament distal end 434 and includes a plurality of key members 452 disposed upon filament 430. Key member 452 also includes deflectable tab 456. Deflectable tabs 456 are similar to deflectable tabs 238 of FIGS. 12-13 described above.

Reshaping cord 460 is attached to filament distal end 434. In one embodiment, a cord ring 436 is disposed at filament distal end 434. Reshaping cord 460 may be as described above for reshaping cord 240. Reshaping cord 460 is disposed within lumen 472 of lock 470 and extends to a control mechanism (not shown) external of the patient for manipulation by the clinician.

Annulus reduction assembly 415 further includes holding tube 480 positioned proximal to lock 470. Holding tube 480 includes lumen 482 through which reshaping cord 460 passes. In one embodiment, holding tube 480 holds lock 470 in place, keeping it from moving in a proximal direction while annulus reduction assembly 415 is formed into a ring shape.

In operation, annulus reduction assembly 415 is delivered to the cardiac valve in a manner as described above in FIG. 2. Annulus reduction assembly 415 is delivered in a straightened delivery configuration. Once at the target valve, the physician begins the implantation by pulling reshaping cord 460 in a proximal direction while at the same time keeping filament proximal end 432 stationary via holding tube 480 to form the general ring structure of the annulus reduction ring 420. The mitral valve is not perfectly circular; the anterior portion of the mitral valve annulus is relatively straight such that the mitral valve annulus approximates a "D" shape. Annulus reduction assembly 415, as shown in FIGS. 4 and 5, may be pre-formed to resemble the "D" shape of the mitral valve.

With annulus reduction assembly 415 deployed adjacent, upon or within the valve annulus, further movement of reshaping cord 460 translates filament 430 within reduction ring 420 so that barbs 435 extend through corresponding exit ports 425 to penetrate the annulus of the target valve, thus anchoring annulus reduction assembly 415 to the valve annulus. Exit ports 425 may be arranged along the outermost perimeter of ring 420, in the plane of the ring 420. Alternatively, exit ports 425 may be arranged adjacent the outer diameter or perimeter of the ring, with ports 224 being oriented at an acute angle directed below the plane of the ring, towards the valve leaflets. Exit ports 425 may be spaced non-uniformly around the perimeter of reduction ring 420, as shown in FIGS. 4 and 5, such that barbs 435 extending from exit ports 425 and into the valve annulus can apply annulus reduction forces to selected locations around the valve annulus.

It may be noted that, in annulus reduction assembly 415, barbs 435 are oriented in a direction opposite to the direction of barbs 212 in the above embodiment of annulus reduction assembly 200. This difference may be accommodated by a dedicated delivery system for each embodiment, which will provide for translating the barbed filament within the reduction ring in the required direction to cause the barbs to extend through the exit ports.

Further movement of reshaping cord 460 draws filament distal end 434 and at least a portion of locking assembly 450 through lock 470 to perform a cinching action that shortens at least one transverse dimension of the ring formed by annulus reduction assembly 415, as illustrated in FIG. 5. With annulus reduction assembly 415 anchored to the valve annulus by implanted barbs 435, the cinching action also shortens at least one transverse dimension of the valve, resulting in the remodeling, or reduction of the valve annulus. The remodeling of the valve annulus brings the valve leaflets closer together to improve the valve's ability to close more normally during systole.

Once the valve annulus is reformed to the desired size and shape, the valve annulus reduction assembly 415 remains locked in the desired configuration. The annulus reduction assembly 415 is locked during translation of locking assembly 450 through lock 470 as the reduction ring and valve annulus are formed to the desired shape and size. Additional translation of filament 430 is not required to lock the annulus reduction assembly 415. The locking mechanism is actuated by the movement of at least one key member 452 through lock 470. As key member 452 passes through lock 470, deflectable tab 456 deflects sufficiently towards filament 430 to pass through lock lumen 472. Once key member 452 passes through lock 470, deflectable tab 456 elastically returns in a radial direction to the non-deflected angular position that can prevent unlocking movement of filament. 430 in the opposite direction.

FIGS. 6 and 7 illustrate another embodiment of a barb assembly 610 and reduction ring 620 for annulus reduction assembly 600. For clarity, parts of annulus reduction assembly 600 have been omitted from FIGS. 6 and 7 and from the description. Barb assembly 610 may be fabricated from thin wall tubing and is sized to fit slidably within lumen 630 of reduction ring 620. Barb assembly 610 includes a plurality of barbs 614 that are integrally formed from, or fixedly attached to outer surface 615. Barb assembly 610 also includes lock members 616 that are integrally formed from, or fixedly attached to outer surface 615 at distal end 618. Reduction ring 620 includes a plurality of exit ports 622 and temporary barb 626 disposed at distal end 628.

Annulus reduction assembly 600 functions similarly to annulus reduction assemblies described above. Barb assembly 610 can be axially translated within reduction ring 620 such that barbs 614 will align with, and extend through corresponding exit ports 622 to penetrate the annulus of the target valve. Lock members 616 cooperate, like a ratchet and pawl, with reduction ring distal end 628 or lock 470 to form an adjustable, one-way lock mechanism. Temporary barb 626 may be incorporated to provide stability during the first stages of the implantation procedure.

Barb assembly 610 and reduction ring 620 include flexibility notches 612 and 624, respectively, for selectively improving the flexibility and formed shape of the implanted annulus reduction device. Flexibility notches 612 and 624 may be thermoformed or cut by laser, knife, hot wire or by any other means known in the art, and are generally arranged in a linear series along the bodies of barb assembly 610 and reduction ring 620, respectively. When assembled, flexibility notches 612, 624 are positioned in opposite directions in relation to each other such that, during ring formation, flexibility notches 612 are generally oriented towards the outside radius of the annulus reduction ring and flexibility notches 624 are oriented towards the inside radius of the annulus reduction ring. During ring formation, flexibility notches 612 open and flexibility notches 624 close. The amount that notches 612, 524 either open or close depends on the desired size and shape of the final implanted annulus reduction device. Barb assembly 610 and reduction ring 620 may be composed of biocompatible metals, polymers or combinations thereof, examples of which were described above. Barbs 614 may be composed of materials such as nitinol, cobalt-based alloy, stainless steel, or combinations thereof.

Figure 8:
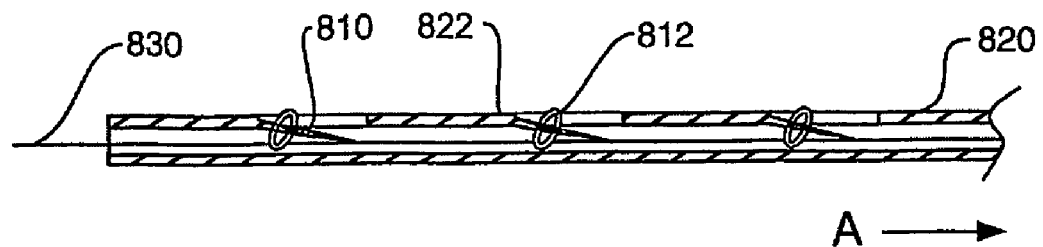
FIGS. 8-10 show detailed views of another reduction ring and barb assembly for a cardiac valve annulus reduction assembly in accordance with the present invention.
Figure 9:
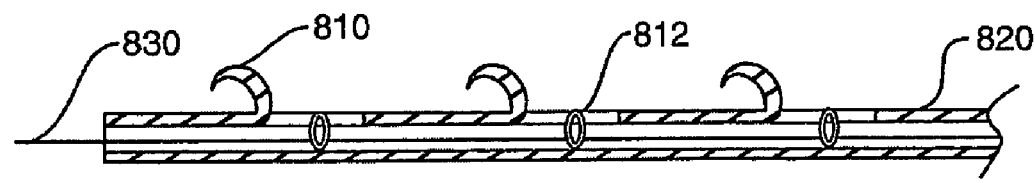
Figure 10:
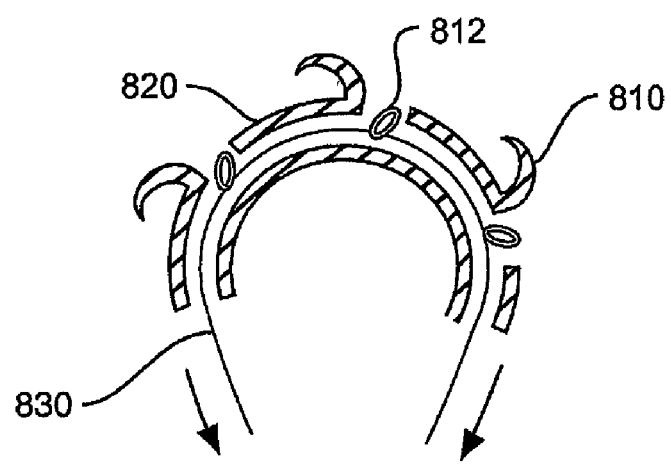

FIGS. 8-10 illustrate another embodiment of an annulus reduction ring assembly 800 in accordance with the present invention. In this embodiment, barbs 810 may be integrally formed with, or fixedly attached to wall 822 of annulus reduction ring 820. In one embodiment, reduction ring 820 is laser-cut in such a manner as to create sharp pointed portions in several locations. These sharp pointed portions may then be shaped, and optionally heat-set into barbs 810. Barbs 810 are composed of a biocompatible material such as nitinol, stainless steel, cobalt-based alloy or combinations thereof. FIG. 8 illustrates that each barb 810 is restrained in a delivery position by a restraining device 812. Restraining devices 812 may be disposed along filament 830, which may be as described above for filament 214. Filament 830 is pulled through reduction ring 820 in the direction of arrow A to slip restraining devices 812 off of barbs 810, thus releasing barbs 810 into their pre-shaped forms. For clarity, FIG. 9 illustrates reduction ring 820 in a straight configuration with barbs 810 in the released position. As described in above embodiments, it will be understood that reduction ring 820 is emplaced within and adjacent to a cardiac valve annulus before anchoring barbs are implanted therein. Referring to FIG. 10, once barbs 810 are released to penetrate the valve annulus, annulus reduction ring 820 can be cinched and locked in the same or similar manner as described above by pulling on elongate member 830.

Figure 11:
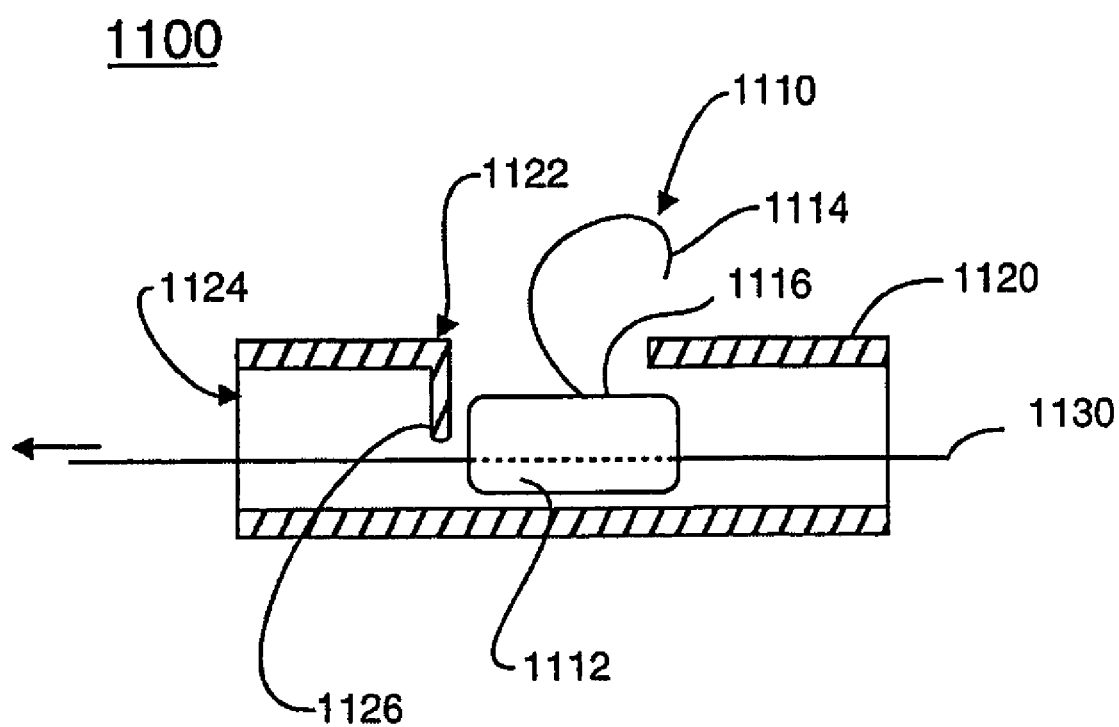
FIG. 11 shows detailed views of another reduction ring and barb assembly for a cardiac valve annulus reduction assembly in accordance with the present invention.

FIG. 11 illustrates another embodiment of an annulus reduction ring assembly 1100 in accordance with the present invention. In this embodiment, reduction ring 1120 includes a stop 1122. Stop 1122 may be formed separately from reduction ring 1120 and attached by welding or adhesive or any other means known to those with skill in the art. Alternatively, a portion of reduction ring 1120 may be cut out and bent down into lumen 1124 to form stop 1122. Stop 1122 extends across lumen 1124 a sufficient length to prevent movement of barb body 1112 beyond stop 1122, but stop 122 provides sufficient clearance to allow unrestrained movement of filament 1130 through lumen 1124. Stop 1122 includes a chamfered or rounded end 1126 for preventing damage to elongate member 1130, which may contact stop 1122. FIG. 11 also illustrates an alternative embodiment of a barb wherein tissue-penetrating portion 1114 of barb 1110 is positioned substantially in the center of top surface 1116 of barb body 1112.

In the previously described embodiments of the invention, damage may occur to a barb extending through an exit port in a reduction ring. Such damage may occur when a filament continues to be pulled with excessive force after a barb impinges on the edge of an exit port. In annulus reduction ring assembly 1100, the use of stop 1122, and optionally the central positioning of tissue-penetrating portion 1114 on barb body 1112, can prevent barb 1110 from potential damage by impingement on the edge of an exit port.

Figure 14:
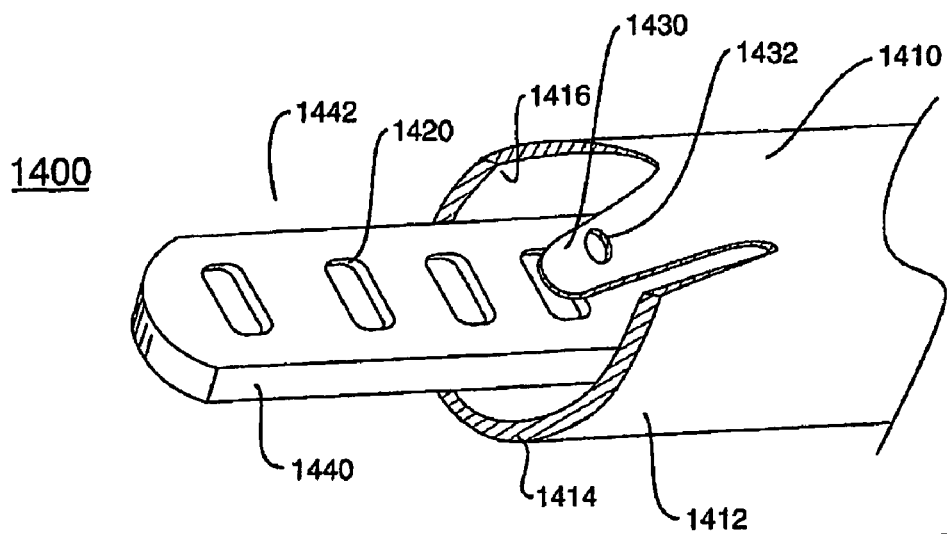
FIGS. 14-16 show detailed views of another lock mechanism for a cardiac valve annulus reduction assembly in accordance with the present invention.
Figure 15:
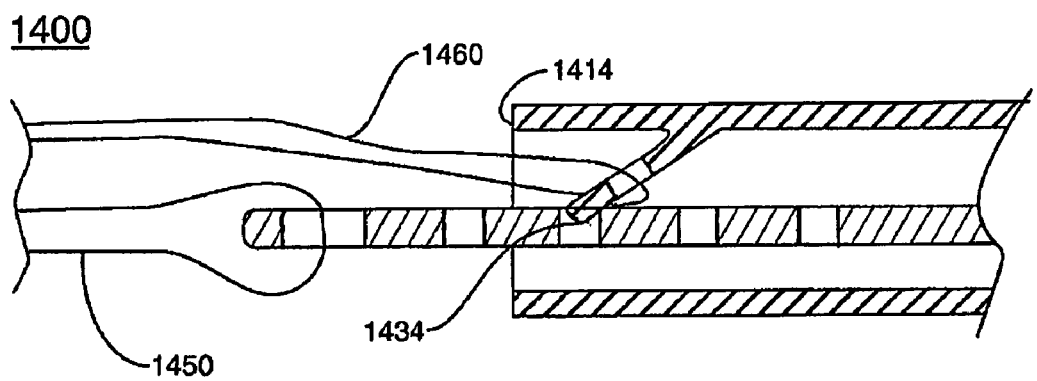
Figure 16:
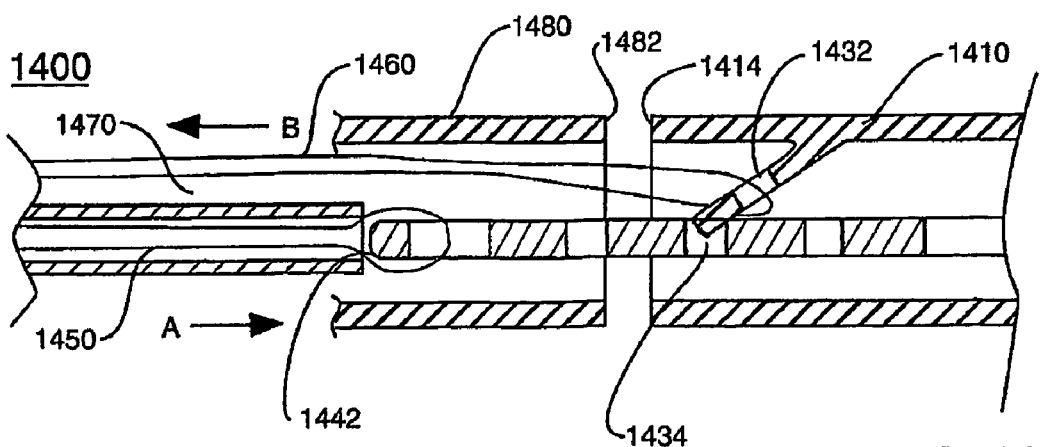

FIGS. 14-16 illustrate another embodiment of a lock mechanism 1400 that may be used in conjunction with the annulus reduction assemblies described herein. FIG. 14 is a perspective view of lock mechanism 1400 and FIGS. 15 and 16 are longitudinal cross-sectional views of lock mechanism 1400. Lock mechanism 1400 comprises tab 1430 disposed at distal end 1412 of annulus reduction ring 1410. A plurality of keyholes 1420 is disposed along distal end 1442 of filament 1440. Filament distal end 1442 may comprise a flattened section of filament 1440 or a separate component attached thereto. Tab 1430 may be formed integrally with reduction ring 1410 or tab 1430 may have been formed separately and attached to reduction ring 1410 by welding, adhesive or by any other attachment method known in the art. Tab 1430 is biased toward lumen 1416 of reduction ring 1410. Tab 1430 includes cord opening 1432 for receiving unlocking cord 1460 in a threaded manner and tip 1434 for insertion into one of keyholes 1420. Locking mechanism 1400 also includes push tube 1470 and lock support tube 1480. Push tube 1470 and lock support tube 1480 may be composed of an incompressible biocompatible metal, polymer or combination thereof that is sufficiently flexible to traverse the vasculature to the target valve.

Referring to FIG. 15, to lock annulus reduction ring 1410 in the reduction configuration, lock support tube 1480 is advanced so that end 1482 abuts end 1414 of reduction ring 1410. Then, while holding lock support tube 1480 in place, lock engagement cord 1450 is pulled to draw filament 1440 through reduction ring 1410 until tip 1434 engages with a selected keyhole 1420 in filament distal end 1442.

Lock mechanism 1400 may be unlocked if desired. Referring to FIG. 16, to unlock the annulus reduction ring, reduction ring 1410 is held in place by lock support tube 1480 as described above. Then, unlocking cord 1460 is pulled in the direction indicated by arrow B to disengage tip 1434 from keyhole 1420. Once lock mechanism 1400 is unlocked, the clinician can readjust the annulus reduction ring and re-lock locking mechanism 1400 as needed. If required, push tube 1470 may be advanced in the direction indicated by arrow A to abut filament distal end 1442. While tip 1434 is held disengaged from keyhole 1420, push tube 1470 may be used to translate filament 1440 proximally into reduction ring 1410 until the desired annulus reduction configuration is formed. Then, unlocking cord 1460 is slackened to allow tab 1430 to engage or re-engage one of keyholes 1420. Lock engagement cord 1450 and unlocking cord 1460 can each be unthreaded and removed by pulling one cord end outside the patient, as described above with respect to other cords.

Figure 17:
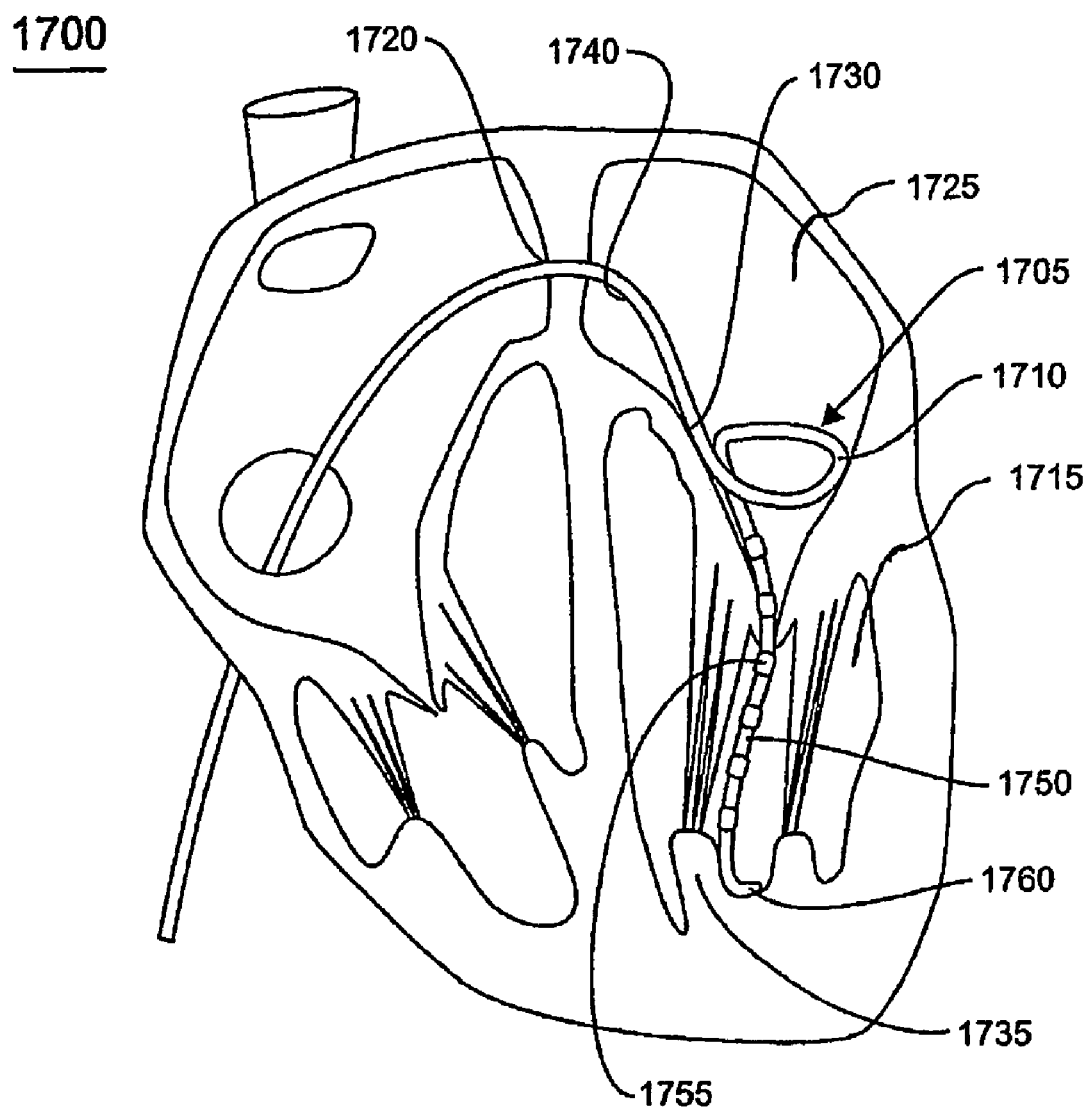
FIG. 17 shows one embodiment of a delivery system for a cardiac valve annulus reduction assembly in accordance with the present invention positioned within the heart.
Figure 18:
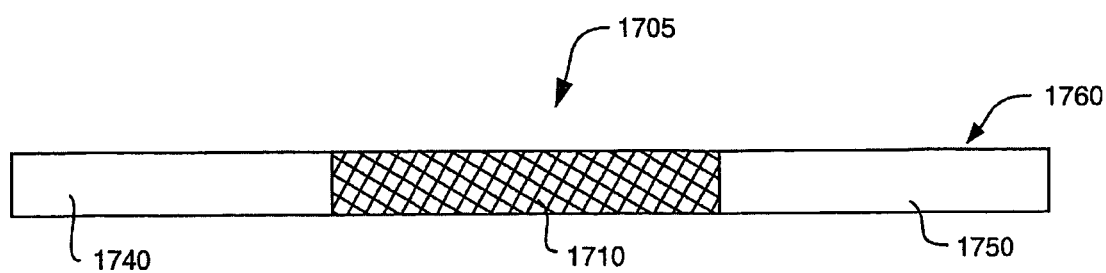
FIG. 18 shows one embodiment of a wireform, shown in a delivery configuration for use in the delivery system of FIG. 17.

FIGS. 17-18 illustrate delivery system 1700 for delivering the annulus reduction systems described herein. Delivery system 1700 comprises wireform 1705 having pre-shaped annular portion 1710, proximal portion 1740 and stabilizer portion 1750. Wireform 1705 may be composed of biocompatible metal, polymer or combinations thereof. In one embodiment, wireform 1705 is pre-shaped and sized to fit the anatomy of a particular patient. In one embodiment, pre-shaped annular portion 1710 comprises nitinol. In another embodiment, pre-shaped annular portion 1710 comprises a section of tubular braid, either with or without a central monofilament core extending there through. Pre-shaped annular portion 1710 provides a rail or guide for positioning an annulus reduction delivery system or device around and within the annulus of mitral valve 1730. FIG. 18 illustrates wireform 1705 in a straight configuration as it may appear either during manufacture and before annular portion 1710 is shaped, or as wireform 1705 may temporarily appear during delivery to a cardiac valve through a delivery catheter.

Wireform stabilizer portion 1750 extends distally from pre-shaped annular portion 1710 and, in one embodiment, extends through mitral valve 1730 and into left ventricle 1715. Stabilizer portion 1750 traverses the left ventricle to rest on or near the apex of the ventricle adjacent papillary muscles 1735 to provide stability for wireform annular portion 1710 during placement of an annulus reduction system. Stabilizer portion 1750 may comprise a material that is relatively soft at distal tip 1760 forming a pigtail or spiral shape as is known in the art. In another embodiment, stabilizing portion 1750 extends from annular portion 1710 in a superior direction to rest against an upper portion of the left atrium 1725 to provide stability. In another embodiment, wireform 1705 does not include stabilizing portion 1750.

Delivery system 1700 provides a pathway to and around the mitral valve annulus for delivering and positioning an annulus reduction assembly for implantation. In one embodiment, delivery system 1700 is delivered to left atrium 1725 through the patient's vasculature in the same or similar manner as described above for delivery of an annulus reduction device. In one embodiment, delivery system 1700 is preceded to the treatment site by a puncture catheter and/or a dilator catheter. Previously described elongate element 132 or delivery catheter 252 may be employed to deliver wireform 1705 to the target cardiac valve.

Figure 19:
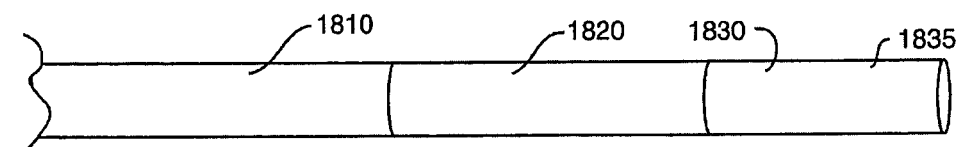
FIG. 19 shows one embodiment of a delivery catheter for delivering the wireform of FIG. 18 to the heart.

FIG. 19 illustrates delivery catheter 1800 for delivering wireform 1705 having a stiff heat-set pre-shaped annular portion 1710. Delivery catheter 1800 includes proximal section 1810, restraining section 1820 and soft distal tip 1830. Delivery catheter 1800 comprises a flexible, biocompatible polymeric material such as polyurethane, polyethylene, nylon, or polytetrafluroethylene (PTFE). Additionally, restraining section 1820 has sufficient stiffening capabilities to maintain pre-shaped annular portion 1710 in a straightened delivery configuration. In one embodiment, a braided metallic or polymeric material is embedded in the wall of restraining section 1820. In another embodiment metallic or polymeric rods are embedded in the wall of restraining section 1820.

In operation, wireform 1705 is inserted into delivery catheter 1800. Delivery catheter 1800 is then advanced to the target valve as described above. In one embodiment, distal end 1835 is positioned within left atrium 1725 and wireform 1705 is pushed out of delivery catheter 1800 to form delivery system 1700 as seen in FIG. 17. In another embodiment, distal end 1835 is advanced through the mitral valve and positioned adjacent papillary muscle 1735. Delivery catheter 1800 is then retracted while wireform 1705 is held stationary. As delivery catheter 1800 is retracted, delivery system 1700 forms as seen in FIG. 17.

Figure 20:
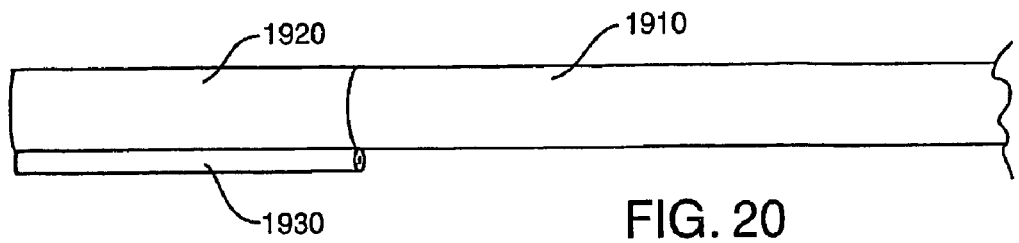
FIG. 20 shows one embodiment of a delivery catheter for delivering a cardiac valve annulus reduction assembly using the delivery system of FIG. 17 in accordance with the present invention.
Figure 21:
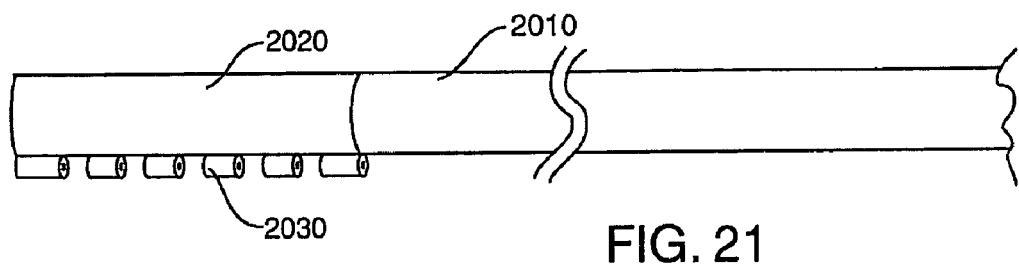
FIG. 21 shows, another embodiment of a delivery catheter for delivering a cardiac valve annulus reduction assembly using the delivery system of FIG. 17 in accordance with the present invention.

Once delivery system 1700 is placed as seen in FIG. 17, delivery system 1700 may be used to guide an annulus reduction delivery catheter to the mitral valve annulus. FIGS. 20 and 21 illustrate two embodiments of annulus reduction ring delivery catheters that may be used with delivery system 1700.

FIG. 20 illustrates annulus reduction ring delivery catheter 1900 having proximal section 1910, distal section 1920 and guide section 1930. Annulus reduction ring delivery catheter 1800 comprises a flexible, biocompatible polymeric material such as polyurethane, polyethylene, nylon, or polytetrafluroethylene (PTFE). Guide section 1930 slides over delivery system 1700 for delivery to the mitral valve annulus 1730. Distal section 1920 comprises a flexible material suitable for traversing rigid pre-shaped annular portion 1710 of delivery system 1700. FIG. 21 illustrates annulus reduction ring delivery catheter 2000 comprising proximal section 2010, distal section 2020 and guide section 2030 similar to that of annulus reduction ring delivery catheter 1900. However, in this embodiment, guide section 2030 comprises a plurality of spaced apart segments for sliding over wireform 1705.

Figure 22:
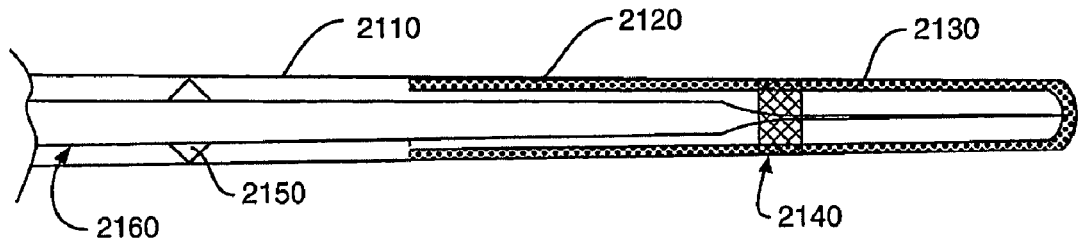
FIG. 22 shows another embodiment of a wireform in a delivery configuration for use in the delivery system of FIG. 17.

FIG. 22 illustrates another embodiment of a delivery system 2100 for delivering an annulus reduction ring to a target valve. Delivery system 2100 comprises outer tube 2110, inner core 2160 and lock 2150. Inner core 2160 includes middle section 2120 and tapered distal portion 2130. Delivery system 2100 further comprises a coil disposed about middle section 2120 and tapered distal portion 2130 for providing flexibility in bending. In this embodiment, the shape of delivery system 2100 is similar to that of delivery system 1700 illustrated in FIG. 17. However, in this embodiment, delivery system 2100 does not include a stabilizing section. In this embodiment, distal portion 2130 forms the annular ring corresponding to pre-shaped annular portion 1710 by mechanical actuation of inner core 2160. Inner core 2160 is attached to the distal end of the coil by soldering, welding, adhesive or other means known in the art. To form the annular portion at the mitral valve annulus, outer tube 2110 is held stationary while inner core 2160 is pulled in a proximal direction. As the inner core is pulled a ring shape forms (not shown) comprising middle section 2120 and tapered distal portion 2130. This actuation mechanism is similar to that of a steerable catheter, as such devices are known in the art. The formed ring can be locked in place using lock 2150. Lock 2150 may comprise a crimp or other type of friction lock. Once locked, delivery system 2100 may be used to guide annulus reduction delivery catheter 1900, 2000 to the mitral valve.

FIG. 23 shows a flow chart for a method 2200 of using cardiac valve annulus reduction system 100 in accordance with the present invention. An exemplary embodiment provides a method 2200 for treating mitral valve regurgitation. Method 2200 will be described with particular reference to the embodiment illustrated in FIG. 3. The method begins by delivering annulus reduction assembly 200 adjacent the mitral valve annulus (Block 2210) using, for example, delivery catheter 252. The annulus reduction assembly can be delivered percutaneously or surgically. Once the delivery catheter is positioned adjacent the mitral valve annulus, annulus reduction assembly 200 is deployed around and within the valve annulus in the ring shape and position intended for implantation (Block 2220). To deploy annulus reduction assembly 200, the clinician holds ring holding tube 254 and retracts delivery catheter 252, and reshaping cord 240 loops cord ring 242 around toward lock 234 to form the intended ring shape. In another embodiment, annulus reduction assembly 200 can be advanced through delivery catheter 252 in order to deploy the device. In another embodiment, annulus reduction assembly 200 is delivered to, and positioned in a ring shape within the mitral valve annulus using delivery system 1700 illustrated in FIGS. 17-19.

Annulus reduction assembly 200 includes barb assembly 210, reduction ring 220, locking assembly 230 and reshaping cord 240 as described above. Upon deployment, barb penetrating members 218 are deployed through exit ports 224 to penetrate the valve annulus (Block 2230). Barb penetrating members 218 are deployed by holding distal end 270 of ring holding tube 254 in contact with proximal end 272 of reduction ring 220 and pulling on actuator cord 258. Pulling on actuator cord 258 translates filament 214 in a proximal direction which allows barb penetrating portions 218 to advance through exit ports 224 and enter the valve annulus to securely anchor within the tissue of the annulus. Ring holding tube 254 may be removed following deployment of barb penetrating portions 218. In one embodiment, prior to deployment of barb penetrating members 218, temporary barb 222 is inserted into the valve annulus to provide a stable position for annulus reduction assembly 200 while initially forming the ring shape and/or during barb deployment.

Next, the clinician reforms the ring shape of annulus reduction assembly 200 (Block 2240). In one embodiment, the ring is cinched, or reformed by holding the position of lock 234 with lock holding tube 256 while pulling reshaping cord 240 in a proximal direction. The reformation of annulus reduction assembly 200 reduces at least one transverse dimension of the ring shape and reshapes the valve annulus as a result of forces applied to the valve annulus tissue by implanted barb penetrating members 218. Thus, the cinching action of annulus reduction assembly 200 causes a reduction in the valve annulus, thus providing for more complete closure of the valve leaflets during systole.

Annulus reduction assembly 200 is locked in the desired configuration by engaging one of key members 232 with lock 234 (Block 2250). As key members 232 pass through lock 234, as described and illustrated in FIGS. 12-13, key members 232 are prevented from backward movement by deflectable tabs 238. This engagement locks the annulus reduction assembly 200 in the annulus reduction configuration. Following the locking of annulus reduction assembly 200, reshaping cord 240 and lock holding tube 256 are removed. Reshaping cord 240 may be removed by releasing a first end of the looped cord and pulling on the second end until the first end exits the patient.

It is important to note that FIGS. 1-23 illustrate specific applications and embodiments of the present invention, and are not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A device for treating mitral valve regurgitation, comprising:
   a tubular member being sufficiently flexible to be transformable between a relatively straight delivery configuration and a deployed ring shape approximating the size and shape of a mitral valve annulus, the tubular member having a through lumen and a plurality of sidewall openings generally disposed around a perimeter of the deployed ring shape; and
   a barb assembly comprising a filament extending through the lumen and a plurality of self-extendible barbs coupled to the filament and corresponding to the sidewall openings, the barb assembly being slidable within the lumen to align the barbs with the corresponding sidewall openings to permit self-extension of the barbs there through; wherein the tubular member has a plurality of protruding anchors generally disposed around a perimeter of the deployed ring shape.

2. The device of claim 1 wherein the filament is a hollow tube.

3. The device of claim 2 wherein the barbs are formed integrally from the hollow tube.

4. The device of claim 2 wherein the hollow tube has a plurality of notches to increase axial flexibility of the barb assembly.

5. The device of claim 1 wherein the tubular member has a plurality of notches to increase axial flexibility thereof.

6. The device of claim 1 wherein the tubular member has a temporary barb disposed at a distal end thereof.

7. The device of claim 1 further comprising a lock mechanism disposed upon the filament for locking the device in the deployed ring shape.

8. The device of claim 7 wherein the lock mechanism comprises:
   a lock disposed at a proximal end of the filament and having a lumen there through, and
   at least one key member disposed at a distal end of the filament and having a key body and a deflectable tab disposed on the key body, the deflectable tab being normally angled away from the filament and being elastically deflectable towards the filament to allow the at least one key member to pass through lock lumen in only one direction.

9. The device of claim 1 further comprising:
   a cord ring disposed at a distal end of the filament; and
   a reshaping cord having first and second ends and being threaded through the cord ring.

10. The device of claim 1 further comprising:
    a stop attached to the tubular member and extending into the lumen, the stop being sized and shaped to prevent movement of the barb in one direction.

11. The device of claim 1 wherein the barbs comprise at least one material from the group consisting of nitinol, cobalt-based alloy, stainless steel, or combinations thereof.

12. A system for treating mitral valve regurgitation, the system comprising:
    a device for treating mitral valve regurgitation in accordance with claim 1;
    a delivery catheter; and
    a locking mechanism disposed upon the filament for locking the device in a reduction configuration.

13. The system of claim 12 wherein the locking mechanism comprises a plurality of locking members securely attached to a distal portion of the filament and a lock attached to a proximal portion of the filament.

14. The system of claim 12 further comprising:
    a wireform having a pre-shaped annular portion for placement adjacent a valve annulus, the wireform comprising a guide for delivering the delivery catheter to the valve annulus.

15. The system of claim 14 wherein the pre-shaped annular portion of the wireform comprises a shape memory material.

16. The system of claim 15 wherein the shape memory material comprises nitinol.

17. The system of claim 16 wherein the wireform further comprises a stabilizer portion extending distally from the pre-shaped annular portion.

18. The system of claim 17 wherein the stabilizer portion has a length sufficient to traverse a heart chamber and to contact a chamber wall opposite a heart valve.

19. The system of claim 17 wherein the wireform includes a soft distal tip.

20. The system of claim 17 wherein the stabilizer portion includes a plurality of radiopaque markers.

21. The system of claim 14 further comprising a wireform delivery catheter.

22. The system of claim 21 wherein the wireform delivery catheter comprises a restraining section for restraining the pre-shaped annular portion of the wireform when the wireform is disposed within the wireform delivery catheter.

23. The system of claim 22 wherein the restraining section of the wireform delivery catheter comprises a braided material embedded in a portion of a wall of the wireform delivery catheter.

24. The system of claim 1 wherein the barbs are composed of a material chosen from a group consisting of nitinol, cobalt-based alloy, stainless steel, or combinations thereof.

* * * * *

UNITED STATES PATENT AND TRADEMARK OFFICE
CERTIFICATE OF CORRECTION

| | | |
|---|---|---|
| PATENT NO. | : 7,655,040 B2 | Page 1 of 1 |
| APPLICATION NO. | : 10/531819 | |
| DATED | : February 2, 2010 | |
| INVENTOR(S) | : Douk et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this

Twenty-third Day of November, 2010

David J. Kappos
*Director of the United States Patent and Trademark Office*